United States Patent
Mayer et al.

(10) Patent No.: US 6,949,672 B2
(45) Date of Patent: Sep. 27, 2005

(54) METHOD FOR PRODUCING ARYLSULPHONIC ACID ISOCYANATES

(75) Inventors: Horst Mayer, Guaratingueta (BR); Dieter Golsch, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/491,420

(22) PCT Filed: Oct. 10, 2002

(86) PCT No.: PCT/EP02/11379

§ 371 (c)(1),
(2), (4) Date: Apr. 1, 2004

(87) PCT Pub. No.: WO03/033459

PCT Pub. Date: Apr. 24, 2003

(65) Prior Publication Data

US 2004/0199011 A1 Oct. 7, 2004

(30) Foreign Application Priority Data

Oct. 11, 2001 (DE) ........................ 101 50 368

(51) Int. Cl.[7] ........................... C07C 263/00
(52) U.S. Cl. .................. 560/344; 560/347; 560/358
(58) Field of Search ............................. 560/303, 330, 560/331, 332, 333

(56) References Cited

U.S. PATENT DOCUMENTS 4,379,769 A    4/1983   Levitt

FOREIGN PATENT DOCUMENTS

| EP | 021 641 | 1/1981 |
| GB | 1 359428 | 7/1974 |
| WO | 199606826 | * 3/1996 |

OTHER PUBLICATIONS

Ulrich et al., Angew. Chem. 78, pp. 761–769 (1966).
Pestycydy 1989, (4), 1–7; ISSN: 0208–8703.
Res. Discl. (1983), 23210, p. 261; ISSN: 0374–4353.
*Journal of Polymer Science*, vol. 13 (1975), p. 267–268.
Database WPI, Sec. CH., Week 198335, Derwent Publications Ltd., London, GB, AN 1983–751010, XP 002227467.

* cited by examiner

*Primary Examiner*—Johann Richter
*Assistant Examiner*—Karl Puttlitz
(74) *Attorney, Agent, or Firm*—Novak, Druce & Quigg

(57) ABSTRACT

The present invention relates to a process for preparing arylsulfonyl isocyanates by reacting an arylsulfonamide with phosgene in the presence of a catalytically effective amount of an alkyl isocyanate.

14 Claims, No Drawings

METHOD FOR PRODUCING ARYLSULPHONIC ACID ISOCYANATES

The present invention relates to a process for preparing arylsulfonyl isocyanates by reacting an arylsulfonamide with phosgene in the presence of a catalytically effective amount of an alkyl isocyanate.

Arylsulfonyl isocyanates are industrially important intermediates in the preparation of a large number of compounds, in particular herbicides. There is a need for processes for preparing them which not only give a high yield and productivity but also display a high reaction rate and thus short reactor occupation times.

U.S. Pat. No. 4,379,769 describes a process for preparing arylsulfonyl isocyanates by phosgenation of arylsulfonamides in the presence of a catalytically effective amount of an alkyl isocyanate and a catalytically effective amount of a tertiary amine base.

In Angew. Chem. 78, pp. 761–769 (1966), H. Ulrich and A. A. R. Sayigh describe the preparation of arylsulfonyl isocyanates, in which either a sulfonamide is reacted with a readily available alkyl isocyanate to form the urea derivative and the latter is subsequently phosgenated, with the starting isocyanate being recovered, or else a catalytic amount of the isocyanate is added to the sulfonamide for the phosgenation.

Pestycydy 1989, (4), 1–7; ISSN: 0208–8703 describes the preparation of 2-chlorobenzenesulfonyl isocyanate by phosgenation of the corresponding sulfonamide in the presence of butyl isocyanats and in ortho-dichlorobenzene as solvent.

Res. Discl. (1983), 23210, p. 261; ISSN: 0374–4353, describes a process for preparing arylsulfonyl isocyanates by phosgenation of arylsulfonamides, in which a mixture of an alkyl isocyanate and an arylsulfonyl isocyanate is used as catalyst. The arylsulfonyl isocyanate formed as product can be recirculated to the reaction in catalytically effective amounts.

Journal of Polymer Science, Vol. 13 (1975), pp. 267–268, teaches the use of a mixture of ortho-dichlorobenzene and cellosolve acetate as solvent in the synthesis of m-phenylenedisulfonyl diisocyanates by phosgenation of m-benzenedisulfonamide in the presence of catalytic amounts of an alkyl or aryl isocyanate.

It is an object of the present invention to provide an improved process for preparing arylsulfonyl isocyanates. The reaction times involved should be very short and/or the formation of undesirable by-products should be minimized.

We have found that this object is achieved by reacting an arylsulfonamide with phosgene in the prescence of catalytically effective amounts of an alkyl isocyanate when the reaction is carried out in the additional presence of a catalytically effective amount of a protic acid or a salt thereof and/or the phosgene is introduced in such a way that the concentration of alkylarylsulfonylurea in the reaction mixture does not go below a minimum concentration during the time of addition.

The present invention accordingly provides a process for preparing arylsulfonyl isocyanates by reacting an arylsulfonamide with phosgene, in which the arylsulfonamide and a catalytically effective amount of an alkyl isocyanate are placed in a reaction zone, forming an alkylarylsulfonylurea as intermediate, and the phosgene is fed into the reaction zone, wherein a) the reaction is carried out in the presemce of a catalytically effective amount of a protic acid which has at least one hydroxy group capable of protolysis or a salt thereof and/or b) the phosgene is introduced in such a way that the concentration of alkylarylsulfonylurea in the reaction zone does not go below 100 ppm during the time of addition.

The process of the present invention is generally suitable for preparing arylsulfonyl isocyanates having unsubstituted or substituted aryl radicals. These are, for example, arylsulfonyl isocyanates of the formula I

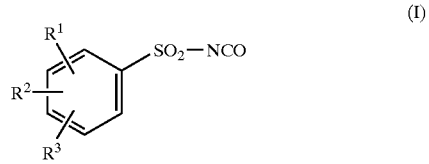

(I)

where $R^1$, $R^2$ and $R^3$ are each, independently of one another, hydrogen or in each case substituted or unsubstituted alkyl, cycloalkyl, heterocycloalkyl, aryl or hetaryl or $WCOOR^a$, $WCOO^-M^+$, $W(SO_3)R^a$, $W(SO_3)^-M^+$, $WPO_3(R^a)(R^b)$, $W(PO_3)^{2-}(M^+)_2$, $WOR^a$, $WSR^a$, $(CHR^bCH_2O)_xR^a$, W-halogen, $WNO_2$, $WC(=O)R^a$ or WCN, where W is a single bond, a heteroatom or a divalent bridging group having from 1 to 20 bridge atoms, $R^a$, $E^1$, $E^2$, $E^3$ are identical or different radicals selected from among hydrogen, alkyl, cycloalkyl, heterocycloalkyl, aryl and hetaryl, $R^b$ is hydrogen or $C_1$–$C_8$-alkyl, preferably methyl or ethyl, $M^+$ is a cation equivalent, $X^-$ is an anion equivalent and x is an integer from 1 to 20, where two adjacent radicals $R^1$, $R^2$ and $R^3$ together with the carbon atoms of the benzene ring to which they are bound may also form a fused ring system having 1, 2 or 3 further rings.

For the purposes of the present invention, the expression 'alkyl' refers to straight-chain and branched alkyl groups. These are preferably straight-chain or branched $C_1$–$C_{20}$-alkyl groups, more preferably $C_1$–$C_{12}$-alkyl groups and particularly preferably $C_1$–$C_8$-alkyl groups and very particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl, nonyl, decyl.

The expression alkyl also encompasses substituted alkyl groups. Substituted alkyl groups preferably have 1, 2, 3, 4 or 5, in particular 1, 2 or 3, substituents selected from among cycloalkyl, aryl, hetaryl, halogen, $NO_2$ CN, acyl, carboxyl, carboxylate, —$SO_3H$ and sulfonate.

The expression cycloalkyl encompasses unsubstituted and substituted cycloalkyl groups. The cycloalkyl group is preferably $C_5$–$C_7$-cycloalkyl group such as cyclopentyl, cyclohexyl or cycloheptyl.

If the cycloalkyl group is substituted, it preferably has 1, 2, 3, 4 or 5, in particular 1, 2 or 3, substituents selected from among alkyl, alkoxy, halogen, NO$_2$, CN, acyl, carboxyl, carboxylate, —SO$_3$H and sulfonate.

For the purposes of the present invention, the expression heterocycloalkyl encompasses saturated, cycloaliphatic groups which generally have from 4 to 7, preferably 5 or 6 ring atoms and in which 1 or 2 of the ring carbons have been replaced by heteroatoms selected from among the elements oxygen, nitrogen and sulfur and which may be substituted. If they are substituted, these heterocycloaliphatic groups can bear 1, 2 or 3 substituents, preferably 1 or 2 substituents, particularly preferably 1 substituent, selected from among alkyl, aryl, alkoxy, halogen, NO$_2$, CN, acyl, COOR$^a$, COO$^-$M$^+$ and SO$_3$R$^a$, preferably alkyl. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl, dioxanyl.

Aryl is preferably phenyl, tolyl, xylyl, mesityl, naphthyl, anthracenyl, phenanthrenyl, naphthacenyl, in particular phenyl or naphthyl.

Substituted aryl radicals preferably have 1, 2, 3, 4 or 5, in particular, 1, 2 or 3, substituents selected from among alkyl, alkoxy, carboxyl, carboxylate, —SO$_3$H, sulfonate, halogen, NO$_2$, CN and acyl.

Hetaryl is preferably pyrrolyl, pyrazolyl, imidazolyl, indolyl, carbazolyl, pyridyl, quinolinyl, acridinyl, pyridazinyl, pyrimidinyl or pyrazinyl.

Substituted hetaryl radicals preferably have 1, 2 or 3 substituents selected from among alkyl, alkoxy, carboxyl, carboxylate, —SO$_3$H, sulfonate, halogen, NO$_2$, CN and acyl.

What has been said above with regard to alkyl, cycloalkyl and aryl radicals applies analogously to alkoxy, cycloalkyloxy and aryloxy radicals.

Halogen is preferably fluorine, chlorine, bromine or iodine, preferably fluorine, chlorine or bromine.

For the purposes of the present invention, carboxylate and sulfonate are preferably derivatives of a carboxylic acid function or a sulfonic acid function, in particular a metal carboxylate or sulfonate, a carboxylic ester or sulfonic ester function or a carboxamide or sulfonamide function. They include, for example, esters with C$_1$–C$_4$-alkanols such as methanol, ethanol, n-propanol, isopropanol, n-butanol, sec-butanol and tert-butanol.

M$^+$ is a cation equivalent, i.e. a monovalent cation or that part of a polyvalent cation which corresponds to a single positive charge. M$^+$ is preferably an alkali metal cation, e.g. Li$^+$, Na$^+$ or K$^+$, or an alkaline earth metal cation, NH$_4^+$ or a quaternary ammonium compound as can be obtained by protonation or quaternization of amines. Preference is given to alkali metal cations, in particular sodium or potassium ions.

X$^-$ is an anion equivalent, i.e. a monovalent anion or that part of a polyvalent anion which corresponds to a single negative charge. X$^-$ is preferably a carbonate, carboxylate or halide, particularly preferably Cl$^-$ or Br$^-$.

x is an integer from 1 to 240, preferably an integer from 3 to 120.

Fused ring systems can be aromatic, hydroaromatic and cyclic compounds joined by fusion. Fused ring systems have two, three or more rings. Depending on the way in which the rings in fused ring systems are linked, a distinction is made between ortho-fusion, i.e. each ring shares an edge or two atoms together with each adjacent ring, and peri-fusion in which a carbon atom belongs to more than two rings. Among fused ring systems, preference is given to ortho-fused ring systems.

The process of the present invention is particularly useful for preparing an arylsulfonyl isocyanate of the formula I.1

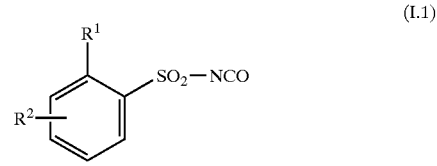

(I.1)

where

R$^1$ is an electron-withdrawing group, preferably a group selected from among F, Cl, Br, NO$_2$, CF$_2$H, CF$_2$Cl$_2$, CHCl$_2$ and CF$_3$, and R$^2$ is hydrogen, C$_1$–C$_4$-alkyl, C$_1$–C$_4$-alkoxy, F, Cl, Br or C$_1$–C$_4$-alkylthio, where the alkyl radicals may bear 1, 2 or 3 halogen atoms.

The sulfonamides used as starting materials can be obtained by reacting the corresponding sulfonyl chlorides with ammonia (M. Quaedvlieg in Houben-Weyl, "Methoden der organischen Chemie", Georg Thieme Verlag, Stuttgart, vol. 9 (1955) 398–400, F. Muth, ibid., 605ff).

The corresponding sulfonyl chlorides for preparing the sulfonamides are generally obtained by a Meerwein reaction (diazotization of suitable amides and sulfochlorinated by means of sulfur dioxide in the presence of copper salts as catalysts: F. Muth in Houben-Weyl, "Methoden der organischen Chemie", Georg Thieme Verlag, Stuttgart, vol. 9 (1955) 579, S. Pawlenko in Houben-Weyl, "Methoden der organischen Chemie", Georg Thieme Verlag, Stuttgart, vol. E 11/2 (1985) 1069), from the corresponding sulfonic acids (F. Muth in Houben-Weyl, "Methoden der organischen Chemie", Georg Thieme Verlag, Stuttgart, vol. 9 (1955) 564), by chlorosulfonation of suitable aromatic precursors (F. Muth, ibid., p. 572) or by oxidative chlorination of low oxidation stage sulfur precursors (mercaptans, diaryl disulfides, S-benzylmercaptans, thiocyanates (F. Muth, ibid., p. 580, S. Pawlenko, loc. cit., p. 1073).

The reaction rate in the phosgenation of arylsulfonamides can advantageously be increased over that in processes known from the prior art when the reaction is carried out in the presence of a catalytically effective amount of a protic acid which has at least one hydroxy group capable of protolysis or a salt thereof.

The amount of protic acid or salt thereof used is preferably from about 0.05 to 1% by weight, particularly preferably from 0.1 to 0.5% by weight, based on the amount of arylsulfonamide used.

Suitable catalysts are generally compounds of carbon, nitrogen, phosphorus and sulfur which have at least one hydroxy group capable of protolysis and the salts thereof. The catalyst is particularly preferably selected from among carboxylic acids, nitric acid, phosphinic acids, phosphonic acids, phosphoric acid and its monoesters and diesters, sulfinic acids, sulfonic acids, sulfuric acid and its monoesters and the salts thereof.

Salts suitable as catalysts are preferably the alkali metal salts, especially the Li, Na and K salts.

Preference is given to using an organic sulfonic acid or a salt thereof, in particular an arylsulfonic acid or a salt thereof, for catalyzing the phosgenation. Particular preference is given to using a benzenesulfonic acid or an alkali metal salt thereof, especially sodium benzenesulfonate.

As an alternative to or in addition to the use of a catalyst in the form of a protic acid or a salt thereof, the reaction rate of the phosgenation of arylsulfonamides can be increased over that of phosgenation processes known from the prior art when the phosgene is introduced in such a way that the alkylarylsulfonylurea concentration in the reaction zone does not go below 100 ppm, preferably 500 ppm, during the time of addition.

The alkylarylsulfonylurea is formed as an intermediate in the reaction zone from the initially charged arylsulfonamide and the alkyl isocyanate used as catalyst. On addition of the phosgene, the intermediate is converted into the arylsulfonyl isocyanate wanted as product and the alkyl isocyanate used as catalyst is reformed.

In a useful embodiment, the introduction of the phosgene is commenced only after the alkylarylsulfonylurea concentration in the reaction zone has reached a value of 100 ppm.

In a further useful embodiment, not only the arylsulfonamide and the alkyl isocyanate but also the alkylarylsulfonylurea derived therefrom are placed in the reaction zone. The amount of alkylarylsulfonylurea initially charged is then at least 100 ppm.

In a preferred embodiment, the introduction of the phosgene is controlled during the time of addition so that the alkylarylsulfonylurea concentration in the reaction zone does not go below the desired value. A volume flow which is less than the maximum volume flow is preferably used at the beginning of the time of addition. A reduced volume flow is preferably used during not more than the first 40% of the time of addition, particularly preferably during not more than the first 30%, in particular during not more than the first 20%. The stream having a flow less than the maximum volume flow can have a flow profile which is increased in the form of a gradient or in one or more steps to the maximum volume flow. Preference is given to using a constant volume flow which is less than the maximum volume flow at the beginning of the time of addition (step profile). The volume flow employed at the beginning of the time of addition is preferably 60%, particularly preferably 50%, of the maximum volume flow. Particular preference is given to a process in which not more than one tenth of the total amount of phosgene is introduced during the first sixth of the time of addition.

Preference is given to using a volume flow less than the maximum volume flow at the end of the time of addition. A volume flow which is less than the maximum volume flow is preferably used during not more than the last 40% of the time of addition, particularly preferably during not more than the last 30%, in particular during not more than the last 20%. The stream having a flow which is less than the maximum volume flow can have a flow profile which is reduced from the maximum volume flow in the form of a gradient or in one or more steps. Preference is given to using a constant volume flow which is less than the maximum volume flow at the end of the time of addition (step profile). The volume flow used at the end of the time of addition is preferably not more than 60%, particularly preferably not more than 50%, of the maximum volume flow. Particular preference is given to a process in which not more than one tenth of the total amount of phosgene is introduced during the last sixth of the time of addition. If the phosgene is added at a constant volume flow rate over the entire time of addition, the time of addition has to be significantly increased over that in the above-described ramp procedure. Otherwise, there is appreciable formation of undesirable by-products such as arylsulfonyl chlorides, which results in a decrease in the yield of isocyanates.

In a particularly preferred embodiment of the process of the present invention, the reaction is carried out in the presence of a catalytically effective amount of a protic acid as described above or a salt thereof and the introduction of the phosgene is also controlled as described above.

The alkyl isocyanate used as catalyst is preferably selected from among $C_4$–$C_{10}$-alkyl isocyanates and $C_5$–$C_8$-cycloalkyl isocyanates, e.g. n-butyl isocyanate, n-pentyl isocyanate, n-hexyl isocyanate, n-octyl isocyanate, n-decyl isocyanate and cyclohexyl isocyanate. Preference is given to using n-butyl isocyanate. The amount of alkyl isocyanate used is preferably in the range from 5 to 40 mol %, particularly preferably from 10 to 30 Mol %, based on arylsulfonamide used.

The amount of phosgene used is preferably in the range from 100 to 250 mol %, particularly preferably from 150 to 200 mol %, based on arylsulfonamide used.

The phosgenation is preferably carried out at from 100 to 175° C. The pressure during the reaction is preferably ambient pressure, but the reaction can also be carried out at elevated or reduced pressures.

Typical reaction times are in a range from about 30 minutes to 24 hours, preferably from 1 to 12 hours.

The reaction is preferably carried out in solvents which are inert toward the starting materials. Such solvents include, for example, aromatic hydrocarbons such as toluene, xylene and mesitylene, haloaromatics such as chlorobenzene, halogenated aliphatic hydrocarbons such as pentachloroethane, etc.

After the reaction is complete, the reaction mixture can be worked up by customary methods known to those skilled in the art. These include, for example, measures for driving off excess phosgene, for example continued heating or passage of a gas stream, for example an inert gas, through the reaction solution. The measures employed for the work-up also include customary methods of separating off the solvent used, e.g. distillation, if desired under reduced pressure. The process of the present invention gives high yields of arylsulfonyl isocyanates and high product purities. The arylsulfonyl isocyanates obtained by the process of the present invention are well-suited to the preparation of herbicides.

The invention is illustrated by the following nonrestrictive examples.

EXAMPLE 1

112.6 g (0.5 mol) of 2-trifluoromethylbenzenesulfonamide, 360 mg of sodium benzenesulfonate and 9.9 g (0.1 mol) of n-butyl isocyanate together with 400 g of ortho-xylene are placed in a 1 l flask provided with a reflux condenser and gas inlet tube and the mixture is heated to an internal temperature of 143° C. 12.2 g of phosgene are fed in at an essential constant volume flow over a period of 2 hours. 63.8 g of phosgene are subsequently fed in at a maximum volume flow over a further period of 120 minutes. A further 11 g of phosgene are subsequently fed in at a constant, reduced volume flow over a period of 2 hours. The yield of 2-trifluoromethylsulfonyl isocyanate was 85% of theory.

EXAMPLE 2 (COMPARISON)

The procedure of Example 1 was repeated, except that 87 g of phosgene were fed in at a constant volume flow over a period of 7 hours. The formation of about 5% of 2-trifluoromethylsulfonyl chloride was detected by means of HPLC, and the yield of 2-trifluoromethylsulfonyl isocyanate was about 80% of theory.

We claim:

1. A process for preparing arylsulfonyl isocyanates, in which an arylsulfonamide and a catalytically effective amount of an alkyl isocyanate are placed in a reaction zone, forming an alkylarylsulfonylurea as intermediate, and phosgene is fed into the reaction zone, wherein
   a) the phosgenation reaction is carried out in the presence of a catalytically effective amount of a protic acid which has at least one hydroxy group capable of protolysis or a salt thereof and/or
   b) the phosgene is introduced in such a way that the concentration of alkylarylsulfonylurea in the reaction zone does not go below 100 ppm during the time of addiction.

2. A process as claimed in claim 1, wherein a protic acid selected from among carboxylic acids, nitric acid, phosphinic acids, phosphonic acids, phosphoric acid and its monoesters and diesters, sulfinic acids, sulfonic acids, sulfuric acid and its monoesters and salts thereof is used in step a).

3. A process as claimed in claim 1, wherein an organic sulfonic acid or an alkali metal salt thereof is used in step a).

4. A process as claimed in claim 1, wherein a phosgene stream having a volume flow which is less than the maximum phosgene flow used is fed into the reaction zone during the first 40% of the time of addition.

5. A process as claimed in claim 1, wherein a phosgene stream having a volume flow which is less than the maximum phosgene flow used is fed into the reaction zone during the last 40% of the time of addition.

6. A process as claimed in claim 1, wherein, in step b), not more than one tenth of the total amount of phosgene is introduced during the first sixth of the time of addition.

7. A process as claimed in claim 1, wherein, in step b), not more than one tenth of the total amount of phosgene is introduced during the last sixth of the time of addition.

8. A process as claimed in claim 1, wherein
   b) the phosgene is introduced in such a way that the concentration of alkylarylsulfonylurea in the reaction zone does not go below 100 ppm during the time of addition, and optionally
   a) the reaction is carried out in the presence of a catalytically effective amount of a protic acid which has at least one hydroxy group capable of protolysis or a salt thereof.

9. A process as claimed in claim 1, wherein
   a) the reaction is carried out in the presence of a catalytically effective amount of a protic acid which has at least one hydroxy group capable of protolysis or a salt thereof, and optionally
   b) the phosgene is introduced in such a way that the concentration of alkylarylsulfonylurea in the reaction zone does not go below 100 ppm during the time of addition.

10. A process as claimed in claim 1, wherein
    a) the reaction is carried out in the presence of a catalytically effective amount of a protic acid which has at least one hydroxy group capable of protolysis or a salt thereof, and
    b) the phosgene is introduced in such a way that the concentration of alkylarylsulfonylurea in the reaction zone does not go below 100 ppm during the time of addition.

11. A process as claimed in claim 1, wherein, in stage (a), the reaction is carried out in the presence of a catalytically effective amount of the salt of the protic acid which has at least one hydroxy group capable of protolysis.

12. A process as claimed in claim 8, wherein, in stage (a), the reaction is carried out in the presence of a catalytically effective amount of the salt of the protic acid which has at least one hydroxy group capable of protolysis.

13. A process as claimed in claim 9, wherein, in stage (a), the reaction is carried out in the presence of a catalytically effective amount of the salt of the protic acid which has at least one hydroxy group capable of protolysis.

14. A process as claimed in claim 10, wherein, in stage (a), the reaction is carried out in the presence of a catalytically effective amount of the salt of the protic acid which has at least one hydroxy group capable of protolysis.

* * * * *

UNITED STATES PATENT AND TRADEMARK OFFICE
CERTIFICATE OF CORRECTION

PATENT NO. : 6,949,672 B2
DATED : September 27, 2005
INVENTOR(S) : Horst Mayer and Dieter Golsch It is certified that error appears in the above-identified patent and that said Letters Patent is hereby corrected as shown below:

<u>Column 7,</u>
Line 14, delete "addiction" and insert -- addition --.

Signed and Sealed this

Twenty-fifth Day of April, 2006

JON W. DUDAS
*Director of the United States Patent and Trademark Office*